United States Patent [19]

Klainer et al.

[11] Patent Number: 4,913,519
[45] Date of Patent: Apr. 3, 1990

[54] OPTICAL SENSOR FOR THE DETECTION OF ICE FORMATION AND OTHER CHEMICAL SPECIES

[75] Inventors: Stanley M. Klainer, San Ramon; Fred P. Milanovich, Lafayette, both of Calif.

[73] Assignee: FiberChem Inc., Las Vegas, Nev.

[21] Appl. No.: 164,172

[22] Filed: Mar. 4, 1988

[51] Int. Cl.$^4$ .................................... G02B 6/02
[52] U.S. Cl. .................... 350/96.29; 250/227.28; 356/417; 340/601
[58] Field of Search ............... 350/96.10, 96.20, 96.29; 250/227; 356/136, 417, 418

[56] References Cited

U.S. PATENT DOCUMENTS

| | | | |
|---|---|---|---|
| 2,359,737 | 10/1944 | Peters et al. | 356/136 |
| 3,540,025 | 11/1970 | Levin et al. | 356/136 |
| 4,410,020 | 10/1983 | Lorenz | 141/65 X |
| 4,608,344 | 8/1986 | Carter et al. | 436/34 |

*Primary Examiner*—William L. Sikes
*Assistant Examiner*—Akm E. Ullah
*Attorney, Agent, or Firm*—Henry P. Sartorio

[57] ABSTRACT

An ice sensor for the remote rapid indication of ice formation or the presence of ice is a fiber optic "switch", activated by ice but not by water, and based on the difference in optical properties between water and ice. The approach is to construct a "fiber optic" which itself is the ice sensor. The fiber optic sensor (FOS) is designed so that no light is transmitted when water is present but as soon as ice begins to form, light is relayed. Thus ice switches on the light! In addition, limited quantitative information can be made available on the rate of ice formation. Alternatively the sensor can be formed of another type optical waveguide instead of an optical fiber. The ice sensor is formed by placing spaced stripes of a clad material on a fiber optic core, or other waveguide structure, where the clad has a refractive index close to ice and the core has an index greater than the clad but less than water. It is best to index match the core to the clad for optimal transmission when ice forms in the gaps between the clad stripes. The advantages of the ice sensor include: specific, sensitive, real-time response, small, light weight, inexpensive, requires no line-of-sight, EMI immune, rugged and flexible. The instrumentation needed to operate the ice FOS is simple, small, light weight, inexpensive, easy to operate, battery powered - optional, rugged, reliable and amenable to telemetry of information.

19 Claims, 2 Drawing Sheets

OPTICAL SENSOR FOR THE DETECTION OF ICE FORMATION AND OTHER CHEMICAL SPECIES

BACKGROUND OF THE INVENTION

The invention relates generally to optical sensors and more particularly to fiber optic and other optical waveguide sensors.

Research and Development on sensors for the detection and quantification of particular chemical species or classes of chemical compounds, is one of the fastest growing technical fields. Yet for all of the effort being expanded, the program is very much fragmented. Each physical or chemical measurement to be made becomes a special project because there is no common ground on which a basic foundation can be laid. Fiber optic chemical sensors (FOCS), CHEMFETs, piezoelectric crystals, semiconductors, etc. require different chemistries (or chemical composition) and sensor design for each specific measurement that is to be made. This means that each time a new target is identified, the research and development effort must start anew.

A new type of sensor as described in U.S. patent application Ser. No. 046,986 has been developed which is adaptable to the analysis of several target molecules or classes of compounds. This would eliminate the need for a large R&D effort for each species to be measured. It is based on the postulation that a custom fiber optic can be made which itself is the sensor. This is done by taking advantage of the relationship between the refractive indices of the core and the clad and how these can be exploited to sense and monitor a species of known refractive index. In this situation, when the target compound interacts with the clad, the optical properties of the sensor change, thus affecting light propagation through the fiber. The light transmission properties which are related to this alteration can be directly related to the analytical information being sought.

Light transmission through a fiber optic is an evanescent wave. If the refractive indexes of air, the core and the clad are $N_0$, $N_1$ and $N_2$ respectively, then the angle at which the light enters the clad, $A_c$, is defined as:

$$A_c = \sin^{-1} N_2/N_1 \quad (1)$$

and the numerical aperture, NA, is dependent on the entrance angle of the light, $A_m$ through the relationship:

$$\sin A_m = NA = (N_1^2 - N_2^2)^{\frac{1}{2}}/N_0 \quad (2)$$

Most important, as to the core of an optical fiber, is that for light to propagate along the fiber, it is required that $N_1 > N_2$.

Areas where the refractive index based sensors should have commercial application include: (i) ice detection, (ii) process control and regulation, (iii) pollution and environmental monitoring, (iv) discovering leaks in pipes and storage tanks and (v) quality inspection of liquids and gases.

The U.S. Air Force, for one, is interested in cooling tower ice detection techniques. Present sensor technology is not compatible with the Air Force's needs for ice detection. In particular, size, specificity, sensitivity and lifetime are requisites that cannot be met with existing devices. Therefore, a completely new, fiber optic sensor technology is desired which has the potential to meet all of the Air Force's requirements. It is also desirable to apply the principles of an ice sensor to detect other chemical species.

SUMMARY OF THE INVENTION

Accordingly, it is an object of the invention to provide an ice sensor.

It is also an object of the invention to provide an optical sensor for the detection of ice formation.

It is another object of the invention to provide an optical sensor based on a fiber optic or other optical waveguide for the detection of ice.

It is still another object of the invention to provide an optical sensor which detects the presence of water and the phase change of water to ice.

It is a further object of the invention to provide an ice sensor for the remote, rapid indication of ice formation or the presence of ice.

It is yet another object of the invention to provide an optical sensor for the detection of other chemical species.

The invention is a fiber optic sensor (ice indicator switch), which uses the differences between the refractive indices of water and ice at 0° C. as the indicator to rapidly, sensitively and specifically identify the presence of ice and/or the onset of ice formation. The invention is based on constructing a custom "fiber optic" which itself is the ice sensor. This new fiber optic "switch" is activated by ice but not by water and is based on the large difference in refractive index of water as it approaches freezing (1.3354) as compared to ice (1.3049). The fiber optic sensor (FOS) is designed so that no light is transmitted when water is present but as soon as ice begins to form, light is relayed. Thus ice switches on the light! In addition, limited quantitative information will be available on the rate of ice formation. Alternatively, the sensor may be implemented with another form of optical waveguide in place of the fiber optic.

The ice sensor is formed by placing a plurality of spaced stripes of a clad material on a fiber optic core or other waveguide. The clad material has a refractive index near that of ice, and the core index is matched to the clad and less than water. In the presence of air, the index of the gaps is that of air and though not optimally matched to the core, some light will be propagated. When the sensor is wet, the gaps are filled with water which has a higher index than the core, so no light is transmitted. However, as the water freezes, and its index drops to optimum index of the clad stripes, maximum propagation occurs.

This device can be constructed using a variety of inorganic, organic and polymeric materials. It is particularly suitable for applications where long-term exposure to adverse (wet and cold) weather conditions are expected. The advantages of the ice FOS include: (i) specific, (ii) sensitive, (iii) real-time response, (iv) small, (v) light weight, (vi) inexpensive, (vii) requires no line-of-sight, (viii) EMI immune, (ix) rugged and (x) flexible. In addition, the instrumentation needed to operate the ice FOS is (i) simple, (ii) small, (iii) light weight, (iv) inexpensive, (v) easy to operate, (vi) battery powered-optional, (vii) rugged, (viii) reliable and (ix) amenable to telemetry of information.

The invention also applies these principles to the detection of other chemical species by forming a sensor with a plurality of clad stripes on a fiber core or other waveguide where the clad stripes have an index close to the index of the desired species and the core is index matched to the clad. When material with an index other than the index of the desired species contacts the sensor and fills the gaps in the clad, light transmission is less than optimal (none if the index is greater than the core). However, when the material contacting the sensor has the desired index, to which the core has been matched, light transmission is maximized.

DETAILED DESCRIPTION OF THE PREFERRED EMBODIMENTS

Figure 1:
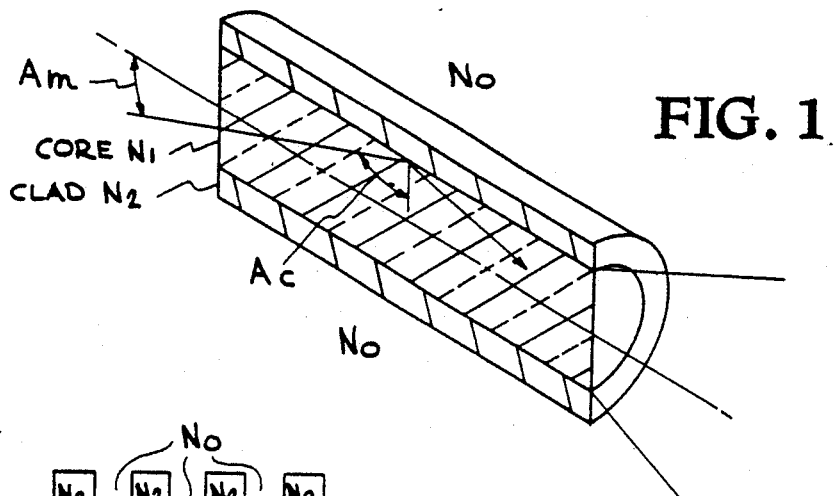
FIG. 1 is an illustration of the operation of a fiber optic to transmit light.

Light propagation through a fiber optic (or an optical waveguide) is dependent on the relationship between the refractive indices of the core and the clad, as previously described and as illustrated in FIG. 1. If the refraction index of the clad is less than that of the core, light is transmitted. If, however, the clad has a higher refractive index than the core, the light exits through the sides and not at the distal end.

Figure 2A:
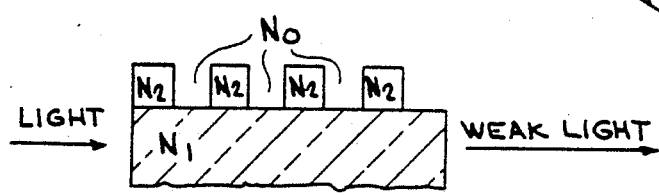
FIGS. 2A,B,C illustrate three operational conditions of an ice sensor according to the invention.
Figure 2B:
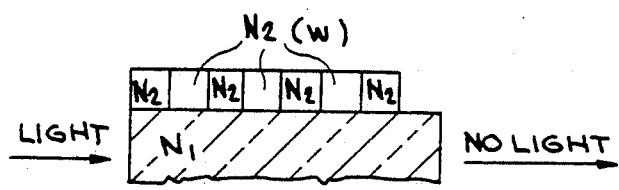
Figure 2C:
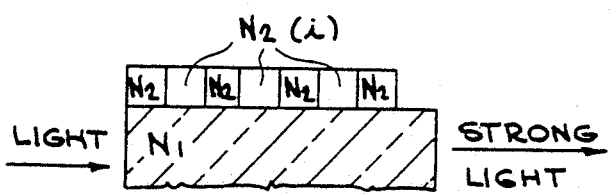
Figure 3:
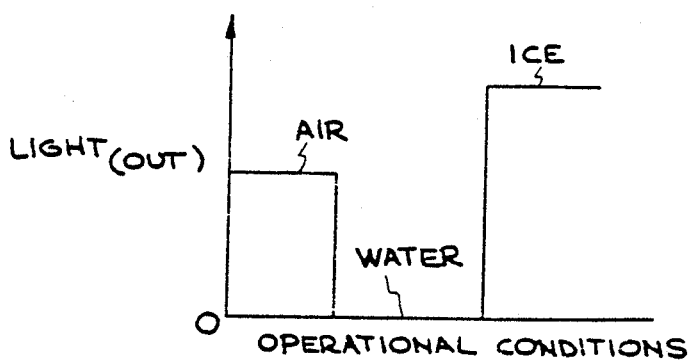
FIG. 3 shows relative signal intensities from an ice sensor.

Fortunately, the refractive index of ice (1.3049) is much less than that of water (1.3354) at 0° C. and both are less than air (1.0003). Thus if a core is selected whose refractive index, $N_1$, is less than 1.3354 [$N_{2(w)}$] but greater than 1.3049 [$N_{2(i)}$], under isolated conditions, no light will be propagated when water is present on the core, while efficient transmission will occur when ice forms on the core. Furthermore, during ice formation, there should be a gradual increase in light intensity, thus signaling the onset to an icing problem. In operation, however, the refractive index of air, $N_0$, plays an active, and important, role because its refractive index is the smallest of all and, therefore, acts as a clad. Accordingly, with only air present there is a fixed known D.C. light propagation. When any water is present, the light guide properties are lost and, consequently, no signal transmission occurs. With ice completely formed, optimum D.C. propagation occurs because the relationship between $N_1$ and $N_{2(i)}$ has been augmented by the proper selection of $N_1$ (index matching). The air response is not as good because $N_0$ is not as good a clad index for the selected $N_1$ as $N_{2(i)}$. The air response is important because it provides a built in test signal which can be checked but only under dry conditions. It does not enter into the picture when rain or ice is present. Thus the information gleaned about the rate of ice formation during the transition from water to ice (or visa versa) is not interdicted by the air. FIGS. 2A-C show the three operational modes of the ice sensor—air, water and ice. Stripes of clad material with index $N_2$ are formed on the core or waveguide of index $N_1$ with $N_2$ equal to the index of ice and $N_1$ optimally chosen for that value of $N_2$. When the gaps between the stripes are filled with air ($N_0$), weak light is obtained. When the gaps are filled with water ($N_{2(w)}$) no light is transmitted. When the water in the gaps freezes to ice, the index changes to $N_{2(i)}$ the same as the stripes, so a maximum light signal is produced. FIG. 3 is a schematic of relative signal intensities expected under these three conditions.

There are two fiber optic ice sensor designs: (i) a fiber optic at the distal end of a standard communications-type fiber optic and (ii) an optical waveguide attached at the end of a communications-type fiber optic. In addition, there are two variations of these: (i) a sensor which is open to the elements and (ii) a sealed device which operates on temperature effects only (requires that ancillary information about weather conditions be provided).

Figure 4:
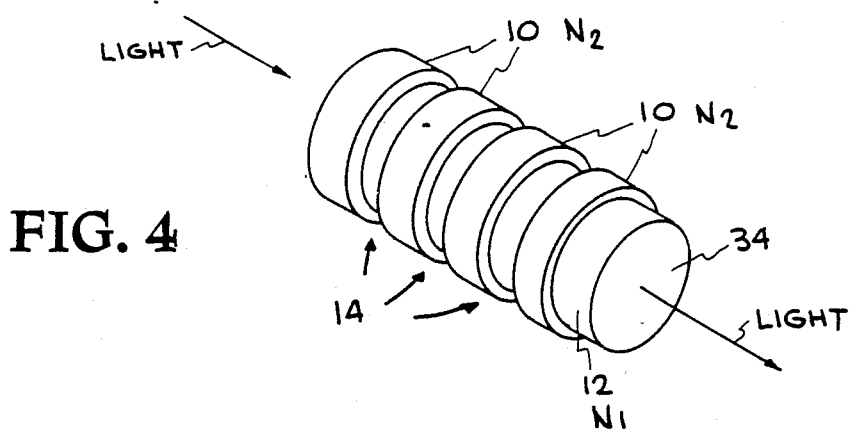
FIG. 4 is a perspective view of a fiber optic ice sensor.

FIG. 4 shows a fiber optic sensor design for direct exposure to the elements. Stripes 10 of clad, whose refractive index ($N_2$) is close to that of ice, are applied to the core 12 at preselected distances from each other. Optimally, these spacings 14 are selected based on the surface tension of water at 0° C. (75.6 dynes/cm) to assure that the water is held in place under wet conditions. Because the clad is discontinuous the only light transmission through the fiber, when no water or ice is present, is due to the refractive index of the air, FIG. 3. When the fiber is exposed to water, the spaces between the clad are filled, air no longer can act as a clad, and no light propagation occurs because water has a higher refractive index than the core (FIG. 3). Under icing conditions, the water between the clad stripes freezes, reducing the refractive index between the stripes to less than the core (and optimally index matched to the core) and efficient light transmission occurs (FIG. 3).

Figure 5:
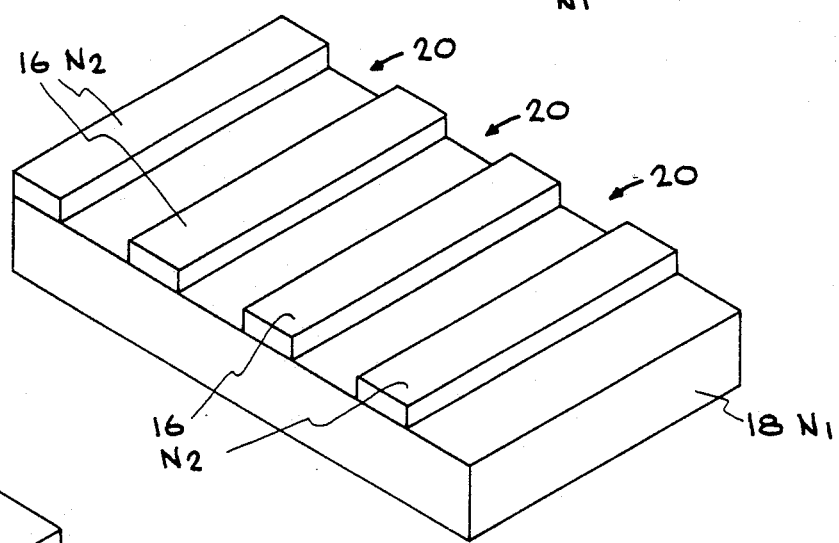
FIG. 5 is a perspective view of a waveguide ice sensor.

A fiber optic is a type of optical waveguide that is often advantageous for a sensor. If larger surfaces areas than can be provided by a fiber optic are desired, then a larger waveguide (FIG. 5) can be substituted for the FOS at the distal end of the standard communications fiber. The general configuration will be similar to the FOS where stripes of clad, separated by specific spacings, are used to help generate a variety of light propagation conditions. A plurality of clad stripes 16 of index $N_2$ are formed on waveguide (substrate) 18 of index $N_1$ with spaces 20 between the clad stripes. The relationship between $N_1$ and $N_2$ and the operation of the sensor are similar to that of the fiber optic configuration.

For selected uses it is possible to enclose each of the above ice sensors in a sealed vessel which contains water. Under these conditions water is always present and an "off/on switch" exists, i.e. no light when the temperature is above freezing and light transmission, starting with the formation of ice, which continually increases to a maximum when complete solidification occurs. The drawbacks to this type of sensor are: (i) it does not give information about whether or not there is water present on the towers to form ice and thus an independent weather report would be needed and (ii) there is no reference (or system check) signal from air under dry conditions. The main reason for using this design is that it is a true switch and consequently, there would be little to no possibility of human error.

The selection of core and clad materials is a key part of forming the sensor A solid, stable, rugged, weather resistant core material with a refractive index >1.3049 but <1.3354 and a clad material with a refractive index very close to 1.3049 are required.

The first step will be to select a core material. This must have a refractive index <1.3354 but >1.3049. In addition, it must be (i) a solid able to withstand the expected temperature extremes, (ii) insoluble in water at all ambient temperatures and (iii) not affected by any pollutants that may be present. The refractive indices are lower than most common compounds. However, a special glass or inorganic compound may be used or else a polymer. The specifications for the core material eliminate most glasses. One preferred material is a pressed core of potassium fluoroborate (KBF$_4$) with a refractive index of 1.325. Potassium fluorosilicate (K$_2$SiF$_6$) may also be suitable with a refractive index of 1.3391. These compounds are essentially insoluble in cold water. Custom made plastics may be more suitable; for example, the polytetrafluoroethylenes can be made with refractive indices from 1.30 to 1.40 depending on such factors as crosslinking, dopants, cure cycles, etc., and thus provide a number of materials with the required index. Cryolite and AlF$_3$ are other materials with an index of about 1.32.

The second step is to find a clad. For optimum sensor performance, the refractive index is critical for the clad. It must be index-matched to that of ice (1.3049). Although, theoretically, the clad should work if it is <1.3354 and >1.0003, a good switch requires a clad whose refractive index is near that for ice. The clad material is preferably a polymer with a refractive index near 1.30. Fluoridated polyurethane (FPU) has an index of about 1.30.

Once the core and clad materials have been selected, it is necessary to place the clad on the core in the desired pattern. Inasmuch as both the distance between each clad stripe and the width of each stripe are critical for optimum performance, accurate, reproducible methods of applying the clad must be used. The stripes themselves cannot act as a clad but must still be close enough so that water is held between them.

Two preferred methods of putting the clad down are: (i) a photo-resist method or (ii) coating the core, where the spaces are wanted, with a material that will not allow the clad to attach. Of these, the photoresist technique is preferred because it is a well established way to accurately put thin films on surfaces. An alternate method is to coat the entire surface and etch or otherwise remove the clad where spaces are desired.

Figure 6:
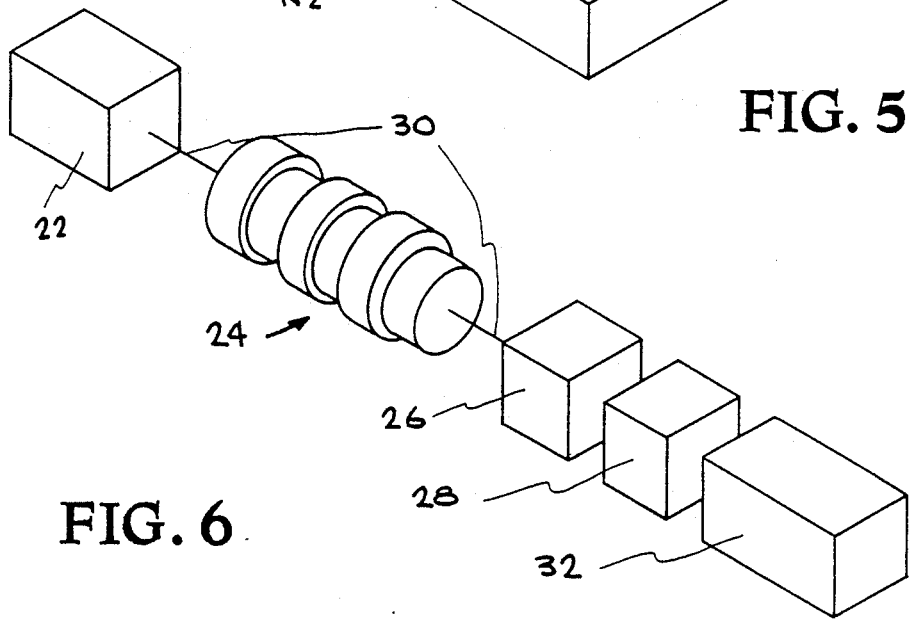
FIG. 6 is a schematic view of an ice sensor system.

These fiber optic (or waveguide) ice sensors are designed so that specificity to ice vs. water is relegated to refractive index matching the sensor components to ice and not to water. Since there is a deliberate mismatch for water, only the amount of light coming out of the fiber needs to be measured to determine the presence of ice. Consequently, it is possible to use a very simple device to make this measurement. As shown in FIG. 6, the "reader" for the ice FOS (or waveguide) would consist of: (i) a LED (or miniature halogen lamp) light source 22, (ii) the sensor 24, (iii) a photodiode detector 26, and (iv) a small hard wired data collection and processing electronics board or package 28. Light source 22 is connected to sensor 24 and sensor 24 is connected to detector 26 by standard fiber optics 30. The system can be packaged so that only the sensor is exposed and all other components are protected from the weather and environment. For multiple sensor operation the choices are: (i) a light source and detector for each sensor; (ii) a single light source feeding several sensors through commercial fiber optics; (iii) transmitting the signal from several sensors over commercial fibers, through a multiplexer and sequencer, to a single detector and (iv) any combination of the above. Optional accessories could include a battery pack, telemetering equipment and a recorder 32 (line or battery operated).

It is also possible to make a single-ended system by putting a light reflector at the end of the FOS so that both the input light and the return signal use the same fiber. This could be implemented by slivering the end 34 of core 12 as shown in FIG. 4. In this configuration the returning light is segregated from the input illumination by a geometric splitter or a dichroic mirror.

Sensing of ice at selected points on the tower support structural members can be accomplished either by: (i) placing a sensor system (source, sensor, detector and electronics) at each location to be monitored and sending the output to a central processing station or (ii) attaching standard fibers (in bundles) to the FOS to transmit light into a number of strategically placed sensors and sending the emitted light back to the detector(s) through other fiber optics. Here the sending and transmitting optics are wrapped around the supporting members to keep the sensors in place. When wrapping the fibers around the support, it may be worthwhile to consider the single-ended system configuration.

The principles of the invention applied to the ice sensor can be generalized to a family of chemical sensors which also form a part of the invention. A fiber optic core or other waveguide is coated with a plurality of spaced clad stripes where the clad has an index $N_2$ near that of the desired species and the core has an index $N_1$ optimally matched to the clad. When material of index other than $N_2$ fills the gaps between the clad stripes, a light signal is decreased or even extinguished. However, when material of the correct index $N_2$ fills the gaps, the light signal is a maximum. One particular application is to detect sugar solutions of a desired concentration. Striped clad of the appropriate index are formed on the core. When the solution has a different concentration, then the index is not correct and light transmission is suboptimum. However, when the desired concentration is present, the index of the clad is optimum and light transmission is maximized. Thus, on the basis of refractive index effects, the striped clad sensor of the invention allows the detection of a particular species, or a certain concentration of a particular species, or even the occurrence of a phase transition of a particular species.

These new approaches to sensor technology have many benefits. Some of the key benefits include: (i) a single technology on which many sensors can be based; (ii) the use of materials which are inherently stable, long-lived and non-polluting; (iii) sensors which are amenable to bulk manufacture at low cost (projected manufacturing cost <$5.00 per sensor); and (iv) readers which are simple, inexpensive, and easy to manufacture (projected manufacturing cost <$300.00 per single sensor unit without telemetry, battery pack and recorder).

Changes and modifications in the specifically described embodiments can be carried out without departing from the scope of the invention which is intended to be limited only by the scope of the appended claims.

We claim:

1. An optical sensor for detecting ice formation, comprising:
    a light guiding means having a refractive index $N_1$ greater than the refractive index of ice at 0° C. and less than the refractive index of water at 0° C.;
    stripes of a clad material having a refractive index $N_2$ substantially equal to the refractive index of ice at 0° C. and formed in a spaced parallel relationship on the light guiding means at a spacing between stripes that is effective to hold water in place when water contacts the sensor.

2. The sensor of claim 1 wherein the light guiding means is a fiber optic core.

3. The sensor of claim 1 wherein the light guiding means is an optical waveguide.

4. The sensor of claim 1 wherein refractive index $N_1$ is matched to refractive index $N_2$ to maximize light transmission through the light guiding means when ice forms on the sensor.

5. The sensor of claim 1 further comprising:
a light source operatively associated with the light guiding means to input light into the light guiding means; detector means operatively associated with the light guiding means to detect light from the light guiding means.

6. The sensor of claim 5 wherein the light source and detector means are connected at opposite ends of the light guiding means.

7. The sensor of claim 5 wherein the light source and detector means are connected at a single end of the light guiding means and the light guiding means further comprises reflecting means at the distal end.

8. The sensor of claim 1 wherein the light guiding means has a refractive index greater than about 1.30 and less than about 1.34 and the stripes have a refractive index of about 1.30.

9. The sensor of claim 1 further comprising a closed housing means filled with water enclosing the light guiding means.

10. A method of detecting ice formation, comprising:
forming an optical sensor of a light guiding means having a refractive index greater than the refractive index of ice at 0° C. and less than the refractive index of water at 0° C. with a plurality of spaced parallel stripes of clad material on the light guiding means, the clad material having a refractive index substantially equal to the refractive index of ice at 0° C., the stripes being spaced at an effective distance to hold water in place when water contacts the sensor;
inputting light into the sensor;
detecting light transmitted through the sensor whereby an intermediate level signal is detected when the sensor is dry and exposed to air, a minimum level signal is obtained when the sensor is wet by water and a maximum level signal is obtained when ice forms on the sensor.

11. The method of claim 10 comprising forming the light guiding means of a fiber optic core.

12. The method of claim 10 comprising forming the light guiding means of an optical waveguide.

13. The method of claim 10 further comprising matching the refractive index of the light guiding means to the refractive index of the clad to maximize light transmission through the light guiding means when ice forms on the sensor.

14. An optical sensor for detecting a chemical species, comprising:
a light guiding means;
stripes of a clad material having a refractive index less than the light guiding means and substantially equal to the refractive index of the chemical species and formed in a spaced parallel relationship on the light guiding means.

15. The sensor of claim 14 wherein the light guiding means is a fiber optic core.

16. The sensor of claim 14 wherein the light guiding means is an optical waveguide.

17. The sensor of claim 14 wherein the stripe width and spacing is effective to be filled by the chemical species or a solution thereof.

18. The sensor of claim 14 wherein the refractive index of the light guiding means is matched to the refractive index of the clad to maximize light transmission through the light guiding means when the gaps between the stripes are filled with a material having a refractive index equal to the clad stripes.

19. The sensor of claim 14 further comprising:
a light source operatively associated with the light guiding means to input light into the light guiding means.
detector means operatively associated with the light guiding means to detect light from the light guiding means.

* * * * *